United States Patent [19]
Speier et al.

[11] Patent Number: 5,868,664
[45] Date of Patent: Feb. 9, 1999

[54] ELECTRICALLY ISOLATED STERILIZABLE ENDOSCOPIC VIDEO CAMERA HEAD

[75] Inventors: Craig Speier; Robert Walls, both of Santa Barbara, Calif.

[73] Assignee: Envision Medical Corporation, Santa Barbara, Calif.

[21] Appl. No.: 606,220

[22] Filed: Feb. 23, 1996

[51] Int. Cl.⁶ ........................................ A61B 1/04
[52] U.S. Cl. ................. 600/112; 600/134; 348/73
[58] Field of Search ................... 600/112, 110, 600/109, 134; 348/65, 73, 75, 82, 373, 374, 376; 250/370.15, 239; 396/535.17

[56] References Cited

U.S. PATENT DOCUMENTS

| | | | |
|---|---|---|---|
| 4,170,997 | 10/1979 | Pinnow et al. | 600/108 |
| 4,590,923 | 5/1986 | Watanabe . | |
| 4,677,471 | 6/1987 | Takamura et al. | 600/110 |
| 4,756,304 | 7/1988 | Watanabe . | |
| 4,831,456 | 5/1989 | Takamura | 348/374 |
| 4,878,485 | 11/1989 | Adair | 600/133 |
| 4,895,138 | 1/1990 | Yabe | 600/110 |
| 4,914,521 | 4/1990 | Adair . | |
| 4,931,867 | 6/1990 | Kikuchi . | |
| 4,977,418 | 12/1990 | Canty | 348/82 |
| 5,010,876 | 4/1991 | Henley et al. . | |
| 5,089,895 | 2/1992 | Fraker et al. | 348/374 |
| 5,428,386 | 6/1995 | D'Alfonso et al. . | |
| 5,536,244 | 7/1996 | Müller et al. | 600/133 |
| 5,587,736 | 12/1996 | Walls | 348/65 |

Primary Examiner—John P. Leubecker
Attorney, Agent, or Firm—Lyon & Lyon LLP

[57] ABSTRACT

A video camera head configured for use with an endoscope and having a conductive inner chamber for shielding the imager and imager electronics from electro-magnetic interference is described in which the inner chamber is substantially isolated from contact by a human or conductive fluid through a sealed outer non-conductive housing. Another aspect of the invention involves hermetically sealing the inner chamber, thus facilitating the use of steam autoclave sterilization, including flash sterilization, to sterilize the camera head.

23 Claims, 6 Drawing Sheets

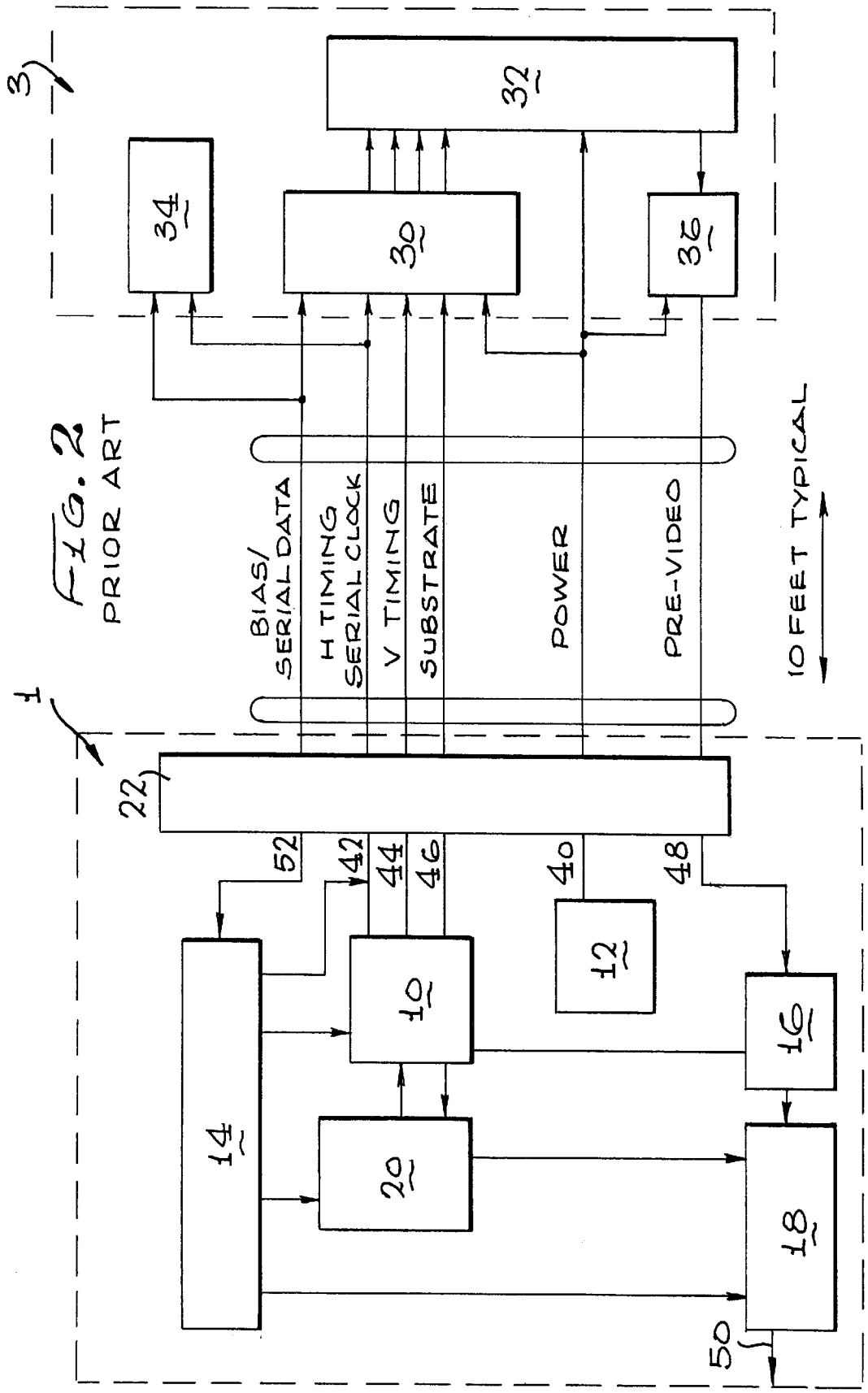

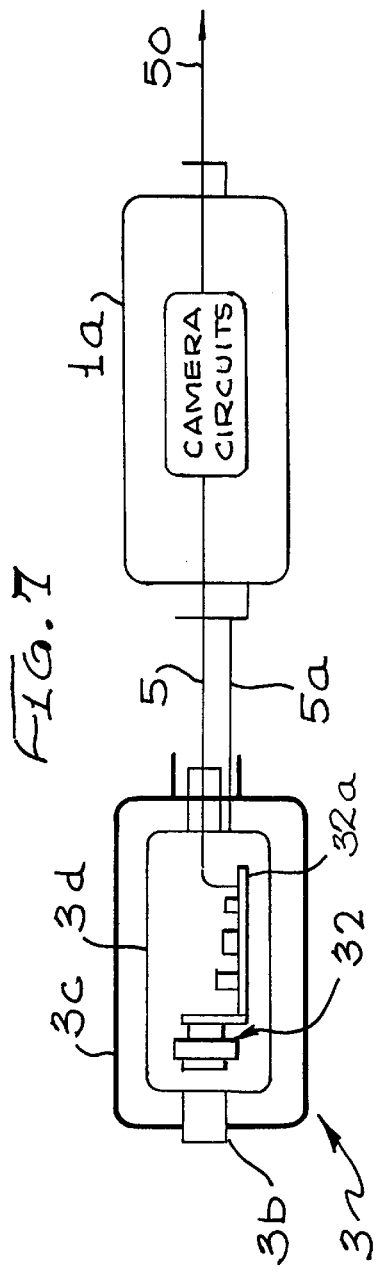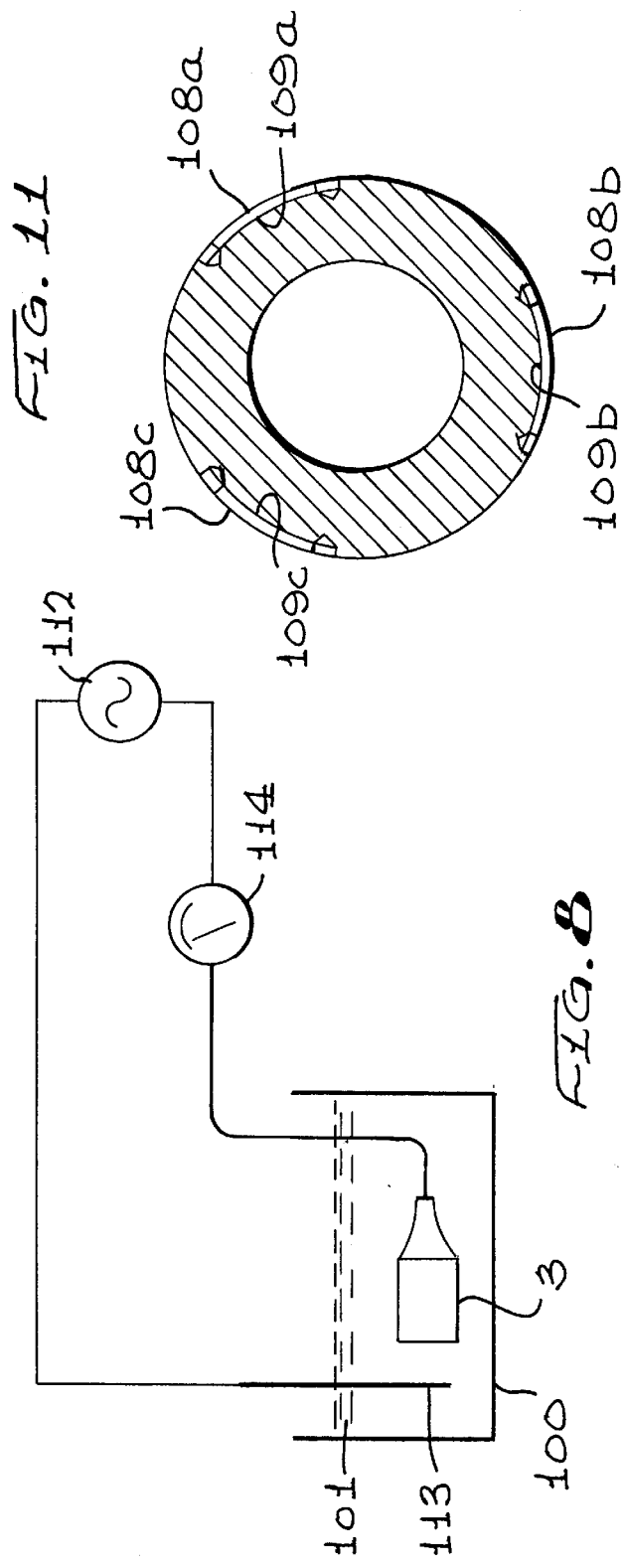

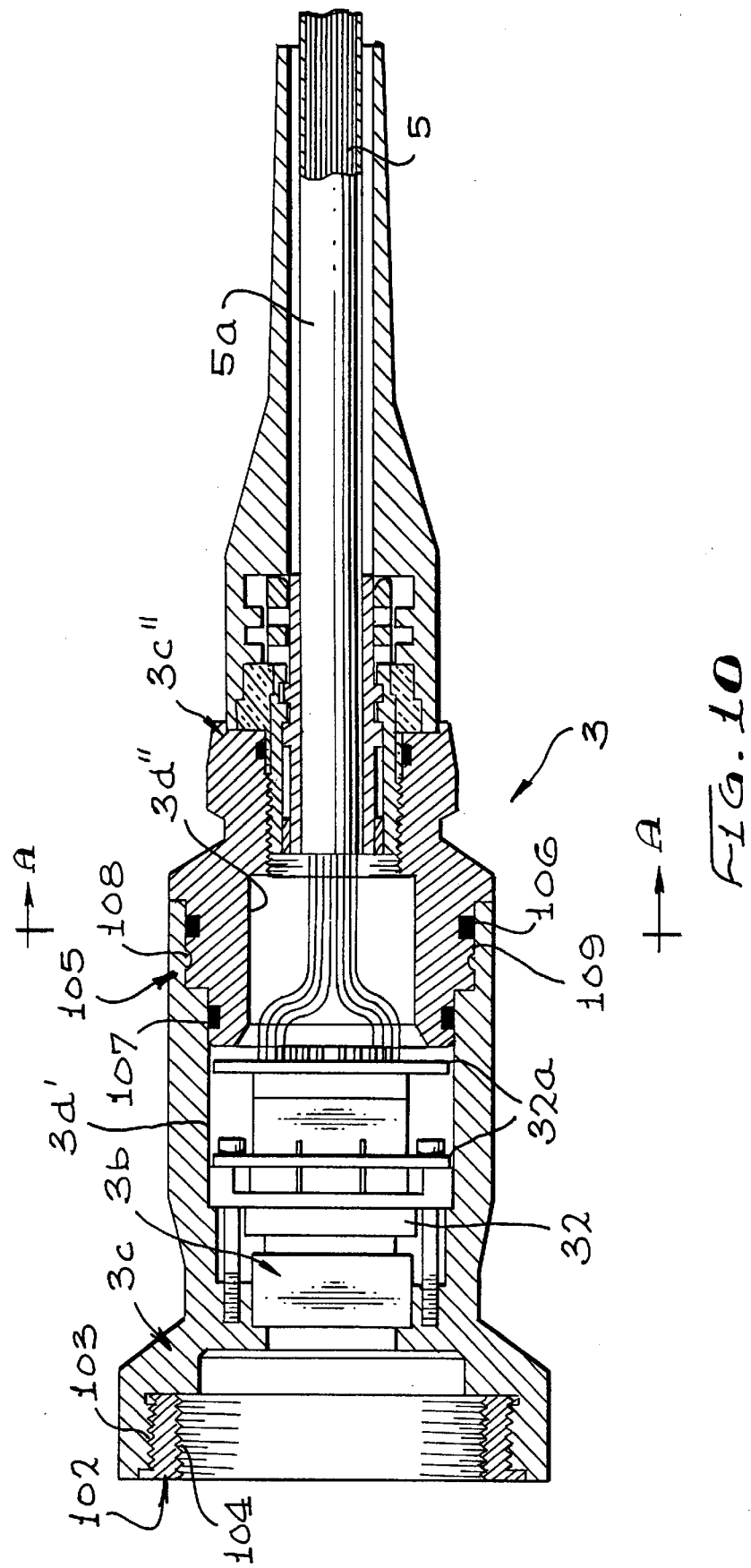

ELECTRICALLY ISOLATED STERILIZABLE ENDOSCOPIC VIDEO CAMERA HEAD

I. BACKGROUND OF THE INVENTION

The field of this invention relates generally to video cameras, and more specifically, to an endoscopic video camera head configured to shield the imager and imager electronics from electro-magnetic interference, to electrically isolate the head from the patient, and to be sterilizable using the steam autoclave process.

In the recent past, the need for small, lightweight video cameras using a solid state image sensor ("imager") such as a charge coupled device ("CCD"), charge injection device ("CID"), or metal oxide semiconductor ("MOS") has rapidly developed for both medical and industrial applications. One medical application involves a video camera attached to an endoscope to allow observation of a surgical site, an internal body structure, or an organ. With a diameter of from 5 to 10 mm., endoscopes are passed into body cavities through small holes to observe structures and perform procedures previously requiring large surgical openings.

In this arrangement, the imager may be contained in a small camera head and attached to the endoscope eyepiece so that the camera head/endoscope combination, or video-endoscope, is lightweight and easily manipulable by a surgeon. A flexible cable connects the camera head to the rest of the camera electronics which are usually included in a camera control unit located remotely from the camera head, and connected via a cable. The camera control unit includes control and video processing circuitry which sends operating signals to the imager and receives signals from the imager which are processed for video display. The camera control unit is also coupled to a video monitor for viewing of the surgical site by one or more physicians. The smallest cameras are made with a single imager but other multiple-imager cameras are also in use, as described in U.S. Pat. No. 5,428,386, which is hereby fully incorporated by reference herein as though set forth in full.

An industrial application employing an imager involves observation of industrial processes in which direct observation by a person is unsafe or otherwise impractical. Such processes include those occurring in nuclear power generating stations, furnaces or engine compartments, or other processes which are generally inaccessible. Here, a camera head including an imager may be attached to a hole in the wall of the vessel in which the process occurs. The camera head is then connected by cable to a camera control unit and video monitor at a remote location in similar fashion to that described above.

Additional background and details regarding video cameras, and their use in medical endoscopic applications, are provided in the following co-pending applications, each of which is assigned to Envision Medical Systems, Inc., and each of which is hereby incorporated by reference herein as though set forth in full:

| Ser. No. | Filing Date | Title |
| --- | --- | --- |
| 08/393,284 U.S. Pat. No. 5,696,553 | February 23, 1995 | REMOTE IMAGER VIDEO CAMERA CABLE COMPENSATION CIRCUITRY |
| 08/458,437 | June 2, 1995 | FIBERSCOPE ENHANCEMENT |
| 08/589,875 | January 23, 1996 | SYSTEM REMOTE CCD VIDEO CAMERA WITH NON-VOLATILE DIGITAL MEMORY |
| 08/018,053 | February 16, 1993 | STERILIZABLE CCD VIDEO CAMERA |

A critical design goal of an endoscopic CCD video camera is electrical safety, both from the standpoint of the operator, and from the standpoint of the patient. Of particular relevance in this regard is the newly adopted safety requirements and regulations of the unified European Community (EC)—the International Electrotechnical Commission, Medical Equipment Particular Standards for Safety of Endoscopic Equipment (IEC 601-2-18)—which are not only becoming common for all Europe, but are finding acceptance world-wide, including within testing agencies in the United States such as the Underwriters Laboratories (UL) standard UL2601. One specific aspect of these safety regulations states that endoscopic equipment that contacts the patient, and in some cases the operator, must be electrically isolated from ground and power sources.

A problem thus arises because most endoscopic video cameras include a grounded metal housing to (1) protect the sensitive CCD imager and associated electronics from susceptibility to externally generated electro-magnetic interference (EMI) and (2) control emissions of electro-magnetic energy generated internally by the camera head circuitry. The need to achieve acceptable electro-magnetic compatibility (EMC), that is, to control electro-magnetic susceptibility and emissions, is quite important. This is especially true in the surgical setting in which there often exists both strong sources of EMI such as electrocautery units and sensitive instruments such as oxygen and $CO_2$ monitors. Moreover, permissible electro-magnetic emission levels are now specified by domestic and international regulation in the same way as other safety standards. In Europe, pursuant to International Electrotechnical Commission IEC 601-1-2, the governing standards are defined by CISPR 11, IEC 801-2, IEC 801-3, IEC 801-4, and IEC 801-5; in the United States, the Food and Drug Administration (FDA) has set forth the applicable standard in MDS 201-0004; and in the United European community (EU), according to an EMC Directive, the governing standards are essentially a composite of the above. In current endoscopic video cameras, this metal housing can easily contact the patient or operator, thus interfering with the objective of achieving compliance with applicable domestic and international safety standards.

Another problem is the difficulty of isolating the patient or user from the power sources used to drive the imager electronics and the camera control unit. Attempts to isolate the camera head from the endoscope by constructing the endoscope eyepiece from a non-metallic material have not proven successful because the limited isolation provided thereby has been easily bridged by the operator's wet hand.

Moreover, there is a growing practice amongst physicians to view images produced by an endoscope on a television monitor, in contrast to viewing these images directly through the endoscope eyepiece. As surgeons have become more comfortable with this practice, the need for the endoscope and imager to be separable at the eyepiece has decreased.

This development has permitted the acceptance of one piece video-endoscopes in which the camera head and endoscope are screwed together or permanently joined, thus allowing for fewer glass interfaces, fewer potential liquid leak paths, and better overall performance. Such a design eliminates the eyepiece, and with it any possible isolation available therefrom by creating a direct connection between the metal endoscope and the metal camera head housing.

Further, known attempts to achieve electrical isolation has not proven successful. For example, Kikuchi, U.S. Pat. No. 4,931,867, describes an approach in which the camera control electronics are segregated into a camera input circuit and a camera output circuit which are isolated from one another through isolation circuitry. This approach is not satisfactory because it allows the camera input circuit and cable shield to float relative to the camera output circuit and video output. Consequently, the potential between this circuitry can become large and induce noise into the sensitive camera circuits. Moreover, electrical isolation between the patient and the metal enclosure of the camera head is not achieved.

Another critical design goal of an endoscopic CCD video camera is sterilizability. Because the camera head and cable are used within the sterile field (an arbitrary area around the surgical site) they must be disinfected like other surgical instruments. The steam autoclave method has long been the preferred method for sterilization, especially for instruments that can withstand the necessary high temperature, 134° C., and the extreme conditions associated with steam sterilization. In the past, instruments such as endoscopic cameras were not thought as being able to withstand the steam autoclave process. Accordingly, these instruments were either treated by less effective means such as cold soak processes or moderate temperature (55° C.) processes, or the camera head and cable were covered with a sterile disposable plastic cover during surgery. Each of these methods has significant disadvantages when compared with the steam autoclave method. For example, the cold soak processes do not achieve the same level of sterility, and the moderate temperature processes involve longer cycle times (2 hours) and the handling and disposal of highly toxic chemicals.

Recently, short exposure steam sterilization techniques have been developed to sterilize instruments more rapidly. One such method, known as flash sterilization, reduces the usual steam autoclave time of 45 minutes to less than 10 minutes by using vacuum evacuation of the steam chamber and elimination of the cloth wrapping procedure that protects the sterilized instruments during storage. The appearance of increasingly virulent contaminates and the need to quickly prepare instruments between procedures has made flash steam sterilization the method of choice for many surgical instruments.

The problem is that many metallic instruments, such as current endoscopic instruments, are usually too hot for immediate use and thus must undergo a cooling-off period. A significant cooling-off period is inconsistent with the objective of efficiently utilizing surgical resources and minimizing equipment or instruments necessary to support an operating room schedule.

Moreover, known attempts to achieve rapid sterilization have not proven successful. For example, Henley, U.S. Pat. No. 5,010,876, describes an approach in which a disposable video camera is used to achieve improved sterility; Adair, U.S. Pat. No. 4,914,521, describes an approach in which a sterilizable video camera cover is applied over a camera to achieve sterile operating conditions; Watanabe, U.S. Pat. No. 4,756,304 describes an approach in which a sterile plastic camera housing is used to cover camera in order to achieve sterility; and Watanabe, U.S. Pat. No. 4,590,923 describes an approach in which a camera is inserted into a metal tubular sterilizable housing in order to achieve sterility. The problem with all these approaches is that they are either uneconomic, cumbersome, or interfere with the objective of achieving electrical isolation of the camera head.

Consequently, it is an object of the subject invention to provide a video camera head configured for use in an endoscopic video camera system which is adequately shielded from EMI and yet is electrically isolated from contact with a human or conductive fluids. Another objective is to provide a video camera head which is readily sterilizable through the steam autoclave process, and which minimizes the cooling-off period required after such a method is employed. Further objects of the invention include utilization of the above concepts alone or in combination. Additional advantages and objects will be set forth in the description which follows, or will be apparent to those of ordinary skill in the art who practice the invention.

II. SUMMARY OF THE INVENTION

To achieve the foregoing objects and advantages, and in accordance with the purpose of the invention as embodied and broadly described herein, there is provided: a video camera head adapted for coupling to a remote camera control unit through a cable having a shield, and also adapted for coupling to an endoscope, comprising: an imager; imager electronics coupled to the imager; a non-conductive outer housing; an inner chamber within the outer housing having a conductive portion which substantially encloses the imager and imager electronics; a first element for electrically coupling one end of a signal line in the cable to the imager electronics; an optical element affixed to a selected one of the housing and inner chamber, and situated along an optical path extending through the housing and the inner chamber to the imager; a second element for electrically coupling the cable shield to the conductive portion of the inner chamber; at least one seal configured to substantially seal any gaps between the optical element and the housing, and between the cable and the housing such that the conductive portion of the inner chamber is substantially isolated from electrical contact with a human or a conductive fluid. An additional embodiment of the subject invention comprises: a video camera head adapted for coupling to a remote camera control unit through a cable, and also adapted for coupling to an endoscope, comprising: an imager; imager electronics coupled to the imager; a non-conductive outer housing; a hermetically-sealed inner chamber within the outer housing which substantially encloses the imager and imager electronics and which comprises an optical element affixed to a conductive portion, wherein the optical element is situated along an optical path extending through the housing and the inner chamber to the imager; a first element for electrically coupling one end of a signal line in the cable to the imager electronics; and at least one seal for substantially sealing any gaps between the housing and the optical element, and between the housing and the cable such that the conductive portion of the inner chamber is substantially isolated from electrical contact with a human or conductive fluid.

III. BRIEF DESCRIPTION OF THE DRAWINGS

FIG. 2 is a block diagram showing a camera control unit and camera head connected together by a cable.

FIG. 7 is a diagram of the preferred embodiment of the subject invention.

FIG. 8 depicts a method for testing isolation in relation to the subject invention.

FIG. 10 shows detail for the floating ring and the snap joint area.

FIG. 11 is a cross-sectional view from line A—A in FIG. 10.

In all the aforementioned figures, like elements are referenced with like identifying numerals.

IV. DESCRIPTION OF THE PREFERRED EMBODIMENTS

Figure 1:
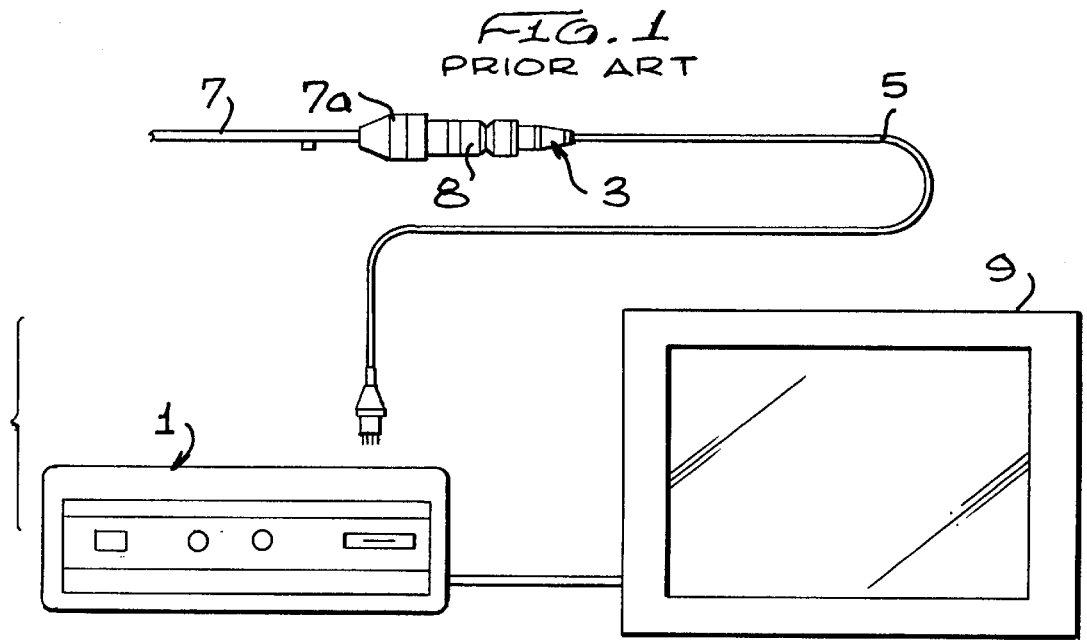
FIG. 1 is a video camera system for use in endoscopy.

Referring to FIG. 1, a video camera system for use in endoscopy is shown. Camera control unit 1 is coupled to camera head 3 by cable 5. Camera head 3 is coupled to eyepiece 7a of endoscope 7 by optical coupler 8. The video signals produced ultimately appear as a video display on monitor 9. Cable 5 may be permanently attached to camera head unit 3 to maintain a tight seal thereby protecting the components contained therein from contaminants. Alternatively, cable 5 may be removably attached to camera head 3. Moreover, as will be discussed in more detail, the camera head 3 may be permanently attached to eyepiece 7a of endoscope 7 or removable therefrom.

Referring to FIG. 2, the camera control unit 1 may include timing signal generator 10, power supply 12, processing means such as a microprocessor 14, sample and hold circuitry 16, process circuitry 18, and sync generator 20. As an alternative, microprocessor 14 may be supplemented or replaced with other suitable processing means such as programmable logic which performs the functions described in connection with microprocessor 14 herein. Camera control unit 1 may also include connector 22 which couples the camera control unit 1 to the cable 5. The camera head unit 3 may include timing driver circuitry 30, solid state image sensor 32 ("imager"), such as a CCD, non-volatile memory device 34 and amplifier 36. Camera head 3 is advantageously small for easy manipulation by a physician in a medical procedure, or for observation of industrial processes providing limited space for the camera head. If a permanent or semi-permanent coupling exists between the camera head 3 and cable 5, the camera head 3 effectively includes the cable 5.

Power supply 12 provides power to the timing driver circuitry 30, solid state imager 32 and amplifier 36 via signal line 40 in cable 5. Timing generator 10 generates H and V timing signals on lines 42 and 44 respectively, as well as a substrate voltage on line 46, which are all sent to the timing driver circuitry 30. Microprocessor 14 or some other processing means provides a bias signal over line 52 to timing circuitry 30. Timing circuitry 30 then provides the bias signal, H and V driving signals and substrate voltage to the imager 32. Imager 32 generates an image, or pre-video signal, which passes through amplifier 36 and returns to the camera control unit 1 through the pre-video line 48. The pre-video signal is then received in turn by the sample and hold circuitry 16 and the processing circuitry 18 which serves to generate a video out signal along line 50 which is sent to other electronics and the video monitor 9.

Microprocessor 14 and sync generator 20 may be coupled to the components of control unit 1 by the various lines of cable 5 shown in FIG. 1. Microprocessor 14 is also coupled to memory device 34 by serial clock line 42 and serial data line 52. Those skilled in the art will recognize that different components and arrangements thereof may be used in addition to and/or in lieu of those shown in the control unit 1 and camera head 3 of FIG. 1.

Figure 3:
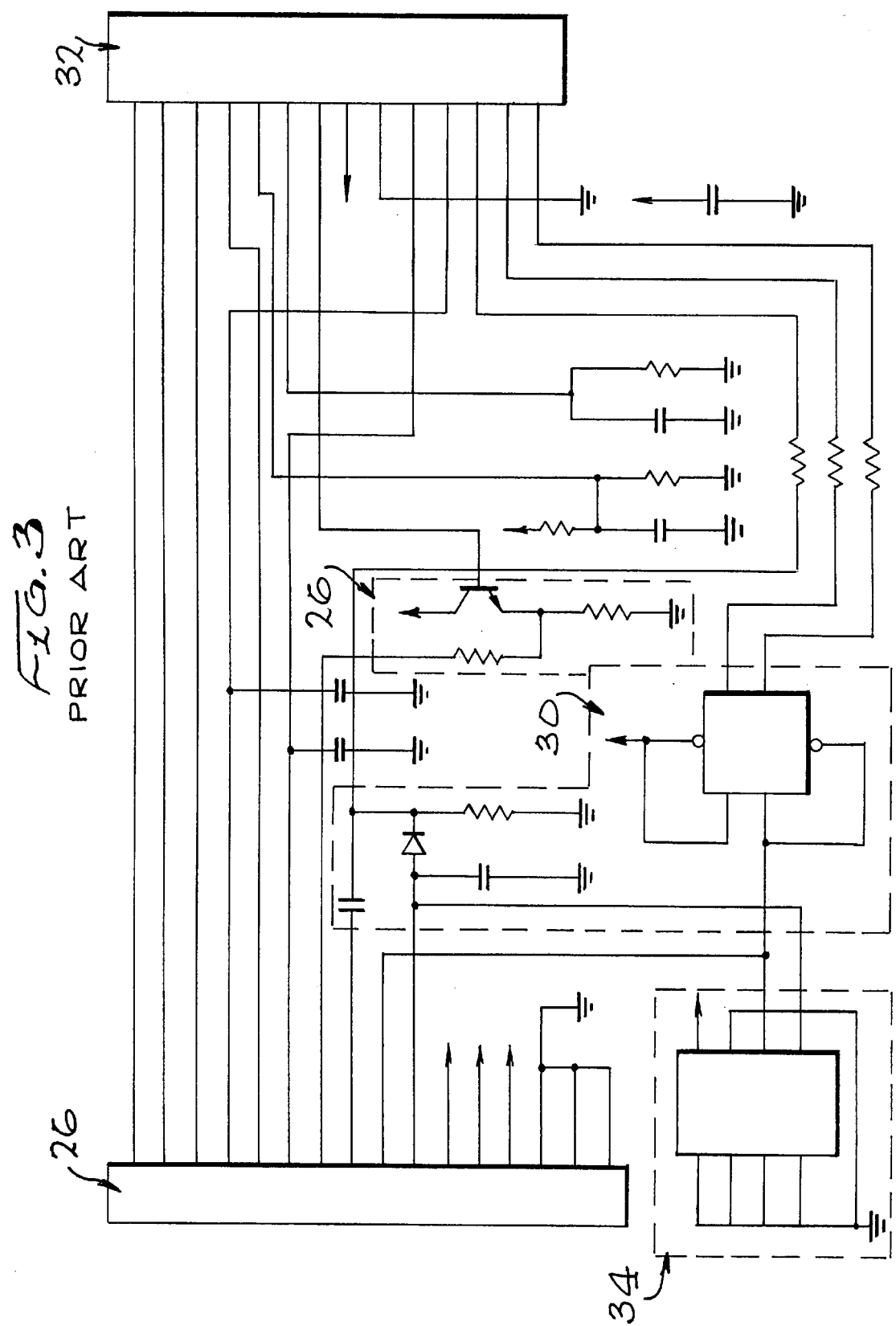
FIG. 3 is a schematic of a camera head.

Referring to FIG. 3, a schematic showing preferred circuitry of camera head 3 is shown. The connector 26 shown in FIG. 3 may be incorporated into the camera head 3 at the location where cable 5 is coupled thereto. Alternatively camera head 3 may not include a connector (e.g., in an embodiment where the cable 5 and camera head 3 are permanently joined), such that connector 26 is contained in control unit 1 as is connector 22 in FIG. 2. The dashed boxes generally represent the memory device 34, timing driver circuitry 30 and amplifier 26.

As shown, the V timing signals V1, V2, V3 and V4 are respectively provided by connector pins 13, 10, 2 and 1 and may pass directly to the imager 32. Alternatively as shown in FIG. 2, the V timing signals may be processed by the timing driver circuitry 30 before passing to imager 32. The substrate voltage, VSUB, is provided by pin 15 and passes directly to the imager 32, or alternatively may first be processed by the timing driver circuitry 30. Power supply signal VL (i.e., typically the lowest voltage supplied by the power supply) is provided by pin 7 and passes to the imager 32. Pin 8 of connector 26 receives the pre-video signal generated by imager 32 after this signal has been processed by amplifier 26 as shown. The PG or pre-charged gate reference signal, against which the actual pixel light values of imager 32 are measured, is provided by pin 9 and is processed by the timing driver circuitry 30 before passing to imager 32.

The H1 timing and serial clock signals are both provided by pin 4. As discussed later, this line-sharing capability is possible because these two signals are preferably transmitted during different phases of the camera system's use. H timing signals which are generally transmitted when the imager 32 operates, are processed by the timing driver circuitry 30 and are then passed to the imager 32. Serial clock signals which are generally transmitted during the turn-on and turn-off phases before and after imager operation, pass directly to the memory device 34. The serial data and bias signals are both provided by pin 5 and also exhibit line-sharing capability in similar fashion.

The +5v, −5v and +15v signals respectively provided by pins 14, 12 and 16 are typical voltages provided by a power supply. In FIG. 3, the −5v line is not used. However, the +5v signal is transmitted to the timing driver circuitry 30 and memory device 34 as well as the other locations shown. The +15v signal is transmitted to the imager 32, amplifier 26 and other locations shown. The PG, H1 and V Shield signals respectively provided by pins 11, 3 and 6 act as shields for the PG, H1 and Video signals. Those skilled in the art will recognize that different component and line configurations may be used.

Figure 4:
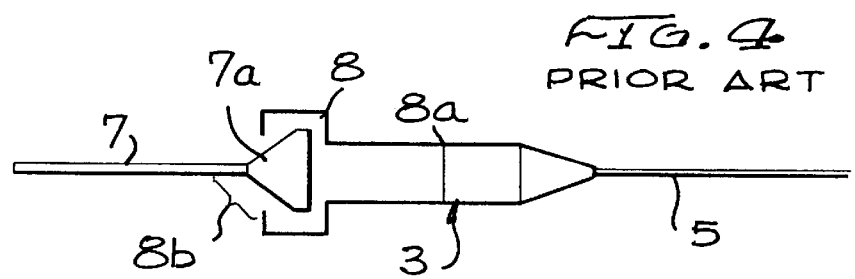
FIG. 4 is a diagram depicting in more detail the coupling between the endoscope eyepiece and the video camera head in the video camera system of FIG. 1.

FIG. 4 shows in greater detail the coupling of an endoscopic video camera head to an endoscope. As shown, endoscopic optical coupler 8 is used to couple the endoscope 7 to the camera head 3. To achieve EMI shielding, the head is typically equipped with a grounded metal enclosure (not shown), and the cable coupling the head to the control circuit is likewise equipped with a shield (not shown). The optical coupler 8 is usually screwed onto the camera head 3 and therefore becomes grounded by contact with the grounded metal enclosure at the thread interface 8a. At the other end of the optical coupler 8, a spring loaded mechanism holds the endoscope eyepiece 7a firmly in place. If the eyepiece material is non-conductive, the endoscope is not grounded by this connection. However, the isolation distance, identified with numeral 8b in the figure, is exposed and easily bridged by the operator's wet gloved hand. Thus, this approach is not usually effective in isolating the patient from ground.

Figure 5:
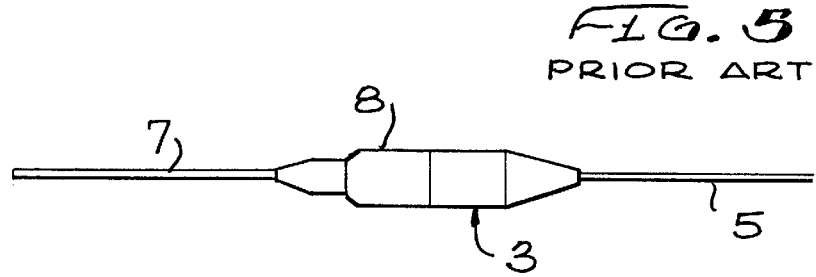
FIG. 5 is a diagram depicting direct coupling between the endoscope eyepiece and the video camera head.

FIG. 5 shows a common alternate configuration and is similar to FIG. 4 except that the endoscope has no eyepiece, thus allowing the endoscope 7 to be directly coupled to the camera head 3 through coupler 8 to improve optical performance, instrument weight, and fogging susceptibility in relation to the FIG. 4 embodiment. The problem, however, is that even the chance of isolation between the endoscope 7 and grounded camera head 3 is eliminated. Thus, this approach is also not effective for the purpose of isolating the patient from ground.

Figure 6:
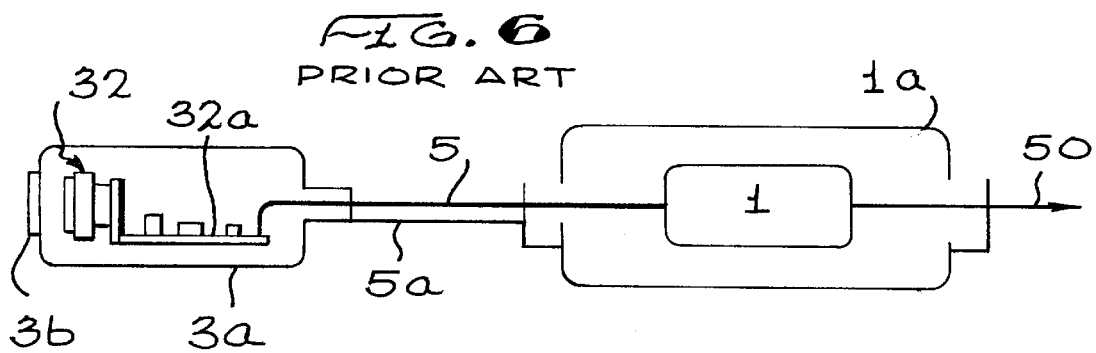
FIG. 6 is a diagram of a video camera system for use in endoscopy in which the camera head, and the camera control unit, are each enclosed with a metallic EMI shield.

FIG. 6 illustrates in more detail the method of EMI shielding used in relation to the embodiment depicted in FIG. 4. As shown, the camera head, comprising imager 32 and imager circuitry 32a, is substantially enclosed by a metallic enclosure 3a having a window 3b which is configured for allowing optical coupling of an endoscope to the camera head. Cable 5 is also sheathed with a cable shield, identified in the figure with identifying numeral 5a, which is electrically coupled to the metallic camera head enclosure 3a. The camera control circuitry 1 is also enclosed with a metallic enclosure, identified in the figure with numeral 1a, which is electrically coupled to the cable shield 5a and thus to the metal camera head enclosure 3a. An insulating jacket (not shown) is also provided which covers the cable shield over its entire length.

Advantageously, the metallic camera head enclosure, the cable shield, and the metal control circuitry enclosure are all referenced to chassis ground and are all configured to form a full shield around the electronics in the system, including imager circuitry 32a and the electronics in camera control unit 1. As dictated by standard video practice, the video output of the unit is also referenced to chassis ground.

A preferred embodiment of the subject invention is illustrated in FIG. 7. As shown in this embodiment, the imager 32 and related electronics 32a are encased by two enclosures. The first, outer housing 3c, is preferably constructed from a nonconductive material, such as plastic. In fact, the use of a plastic outer covering is particularly advantageous in that it facilitates the handling of the camera head following steam sterilization. Plastic conducts heat poorly (low heat conductivity) and so it feels cooler than a metal enclosure. This is because less heat can flow to the skin even though the camera head is actually just as hot. The second, inner chamber 3d, is preferably made from a conductive grounded material to act as an EMI shield.

The inner chamber 3d is electrically coupled to the cable shield 5a to fully enclose the camera head circuits. It is made by either plating a metal to the inside of the nonconductive outer housing 3c, by painting a non-conductive coating on the inside surface of the outer housing, by laminating a metal layer thereto, by inserting a liner between the outer housing and the CCD and related electronics, or simply by covering a pre-existing conductive enclosure with a second non-conductive enclosure. The camera control unit 1 is enclosed by a conductive enclosure 1a which is electrically coupled to the cable shield 5a and to the video output ground. Consequently, in this embodiment, the inner layer 3d, conductive enclosure 1a, and cable shield 5a are all coupled to one another, and to chassis ground.

An optional metal ring (not shown in FIG. 7) is embedded in the nonconductive outer housing 3c near the window 3b to provide means to optically couple the camera head to the endoscope through an optical coupler (see FIGS. 4 and 5). This ring is completely "floating" in the outer housing and so does not compromise the isolation performance in any way.

FIG. 10 provides additional detail on the construction of camera head 3. As shown, ring 102 is completely embedded in non-conductive housing 3c'. This ring has threads on the outside, identified with numeral 103, to hold it in the non-conductive housing 3c', and inside threads, identified with numeral 104, for attachment of a lens or other optical component of an optical coupler.

As shown, the outer housing is advantageously constructed in two parts, identified with numerals 3c' and 3c" to facilitate installation of the imager and imager electronics. An inner conductive chamber 3d' is provided within the outer housing 3c' which chamber substantially encloses imager 32 and imager electronics 32a. Housing 3c" has an inner surface substantially coated with a conductive coating 3d." Electrical coupling between coating 3d" and chamber 3d' is provided by conductive gasket 107. Moreover, cable shield 5a is electrically coupled to conductive coating 3d". Together, the inner chamber 3d', the conductive coating 3d", the cable shield 5a, and the gasket 107 form a complete EMI shield for the imager 32 and related electronics 32a. The cable shield 5a terminates to ground and circuit common at the control unit (not shown).

A snap joint, identified with numeral 105, releasably engages the first and second parts to one another through mating sections 108 and 109. Elastomer O-ring 106 is provided to seal the joint and prevent entry of conductive fluids.

FIG. 11 illustrates additional detail about mating sections 108 and 109. This figure illustrates the cross-sectional view from the line A—A depicted in FIG. 10. As shown, mating section 108 advantageously comprises three coaxially spaced elements 108a, 108b, and 108c, while mating section 109 similarly comprises three coaxially spaced elements 109a, 109b, and 109c.

Because there may be conductive liquids present, the non-conductive housing must as a whole be entirely liquid tight to substantially isolate ground and power sources from electrical contact with a human or conductive fluids. FIG. 8 shows a preferred method for testing isolation to conductive liquids. As indicated, the approach involves providing a container 100 of conductive liquid 101, and configuring a voltage source 112 to apply a voltage across camera head 3 while inserted in the conductive liquid. Advantageously, the voltage is applied by coupling one lead of the voltage source 112 to a connector plate 113 which is inserted in the conductive liquid, and the other lead of the voltage source to the camera head circuitry 32a, while inserted into the liquid. Advantageously, a microamp meter 114 is also provided in order to measure leakage current through the camera head.

The method involves applying a specified voltage to the head, and then measuring leakage current. As specified by section 19 of International Electrotechnical Commission, Medical Electric Equipment, General Requirements for Safety IEC 601-1, the current passing through the head must be less than 50 microamps at 250 volts AC. Moreover, as specified by section 20 of International Electrotechnical Commission, Medical Electrical Equipment, General Requirements for Safety IEC 601-1, the dielectric strength must be such that application of a 2500 volt potential cannot create a breech in the isolation. A "breach" is defined by relevant safety standards as 25 milliamps of current flow at 2500 VAC. The testing device diagrammed in FIG. 8 can be used for this test if the applied voltage is 2500 VAC rather than 250 VAC.

Figure 9:
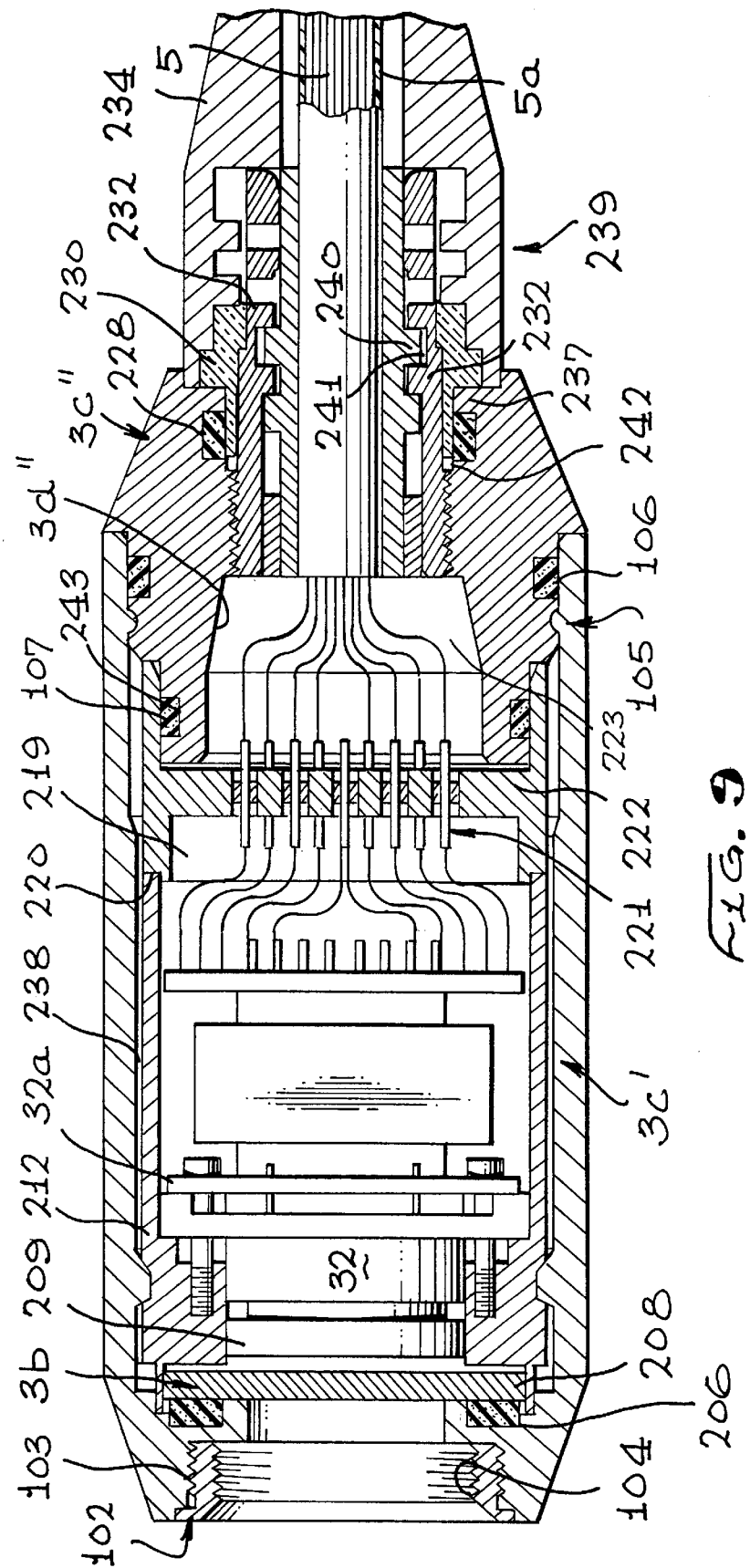
FIG. 9 depicts an alternate embodiment with a sealed inner chamber to facilitate sterilizability of the endoscopic camera.

FIG. 9 shows an alternate preferred embodiment of the subject invention. As shown, the outer housing 3c comprises a first section 3c' and a second section 3c" releasably coupled together through snap-lock arrangement 105. The imager 32 and associated circuitry 32a are located within a hermetically sealed conductive inner chamber 219 comprising bulkhead 222, inner housing 212 and window 3b. Electrical feed-through conductors or first element 221 couple the cable 5 to the imager electronics 32a. Advantageously, the bulkhead 222 and inner housing 212 are titanium and the window is sapphire. Moreover, the window 3b is preferably brazed to the inner housing 212 at circular joint 208. The inner housing 212 at this braze joint 208 is advantageously configured as shown to allow flexibility during the thermal fluctuations of the braze and sterilization processes. The bulkhead 222 is advantageously joined to the inner housing 212 at weld joint 220, which is formed using electron beam welding. Prior to welding, the imager 32 and associated circuitry 32a are advantageously installed into the inner housing 212 and electrical connection is established thereto by means of the inner feed through conductors 221. To extend the useful life (number of steam sterilization cycles), a moisture absorbing desiccant material can be placed within the sealed interior chamber prior to welding. An infrared filter 209 is configured to fit between the imager 32 and the inside of the window 3b. This filter 209 may also include a blur filter component to prevent aliasing artifact on finely detailed images.

Advantageously, inner chamber 219 threads into the first portion 3c' of the outer housing, which is preferably made of a temperature resistant thermoplastic such as polyetherimide (trade name ULTEM) plastic. Alternatively, a snap or glue joint could replace the threads for this attachment. O-ring 206 seals the outside surface of the window 3b to keep liquids from entering the space 238 between the inner chamber 219 and first portion 3c' of the outer housing to maintain electrical isolation. Threaded ring insert or third element 102 has outside threads 103 for attachment to the first portion 3c' of the outer housing and inside threads 104 to serve as the attachment interface for various optical devices (such as an optical coupler shown in FIGS. 4 and 5) that focus an image onto the imager. If thread start alignment is needed, a snap joint or glue joint could be used to attach the thread ring insert 102 to the first portion 3c' of the outer housing. In any event, threaded ring insert 102 is configured to be entirely contained within the plastic outer housing 3c'.

The second portion 3c" of the outer housing releasably attaches to the first portion 3c' at snap joint 105. O-ring 106 seals liquid from entering the space 238 between inner chamber subassembly 219 and the first portion 3c' of the outer housing. A snap joint is used for this attachment because, unlike a thread, it does not need any rotation for engagement. This is important since the wires from the cable 5 are typically connected to the back of the bulkhead 222 at the point just before the second portion 3c" is coupled to the first portion 3c'. Alternatively, a suitable glue could be used for this attachment, in the case in which non-destructive disassembly is not anticipated.

The cable 5 terminates at the second portion 3c" of the outer housing at a cable termination 239, comprising over mold 234 and a two part strain relief comprising elements 230 and 232. The inner portion 232 of the strain relief or second element is advantageously aluminum for strength and electrical conductivity. It forms an extension of the outer conductive shield 5a of the cable 5 and includes male threads 240 for attachment to the second portion 3c" of the outer housing. As shown, this portion is configured with female threads 241 which mate with corresponding ones of male threads 240 of the inner portion 232 of the strain relief. The outer portion 230 of the strain relief preferably contacts the sealing O-ring 228 to keep liquids from entering in the space 242 between the second portion 3c" of the outer housing and the cable assembly. It is also preferably made of a non-conductive material to prevent potentially conductive liquids from contacting the inner portion 232 of the strain relief. The internal signal lines or wires of the cable 5 are connected to the glass insulated feed- through conductors 221 which extend through the bulkhead 222. A moisture sealant or potting process protects the exposed connections between the cable wires and the feed-through conductors 221 in the space 223 to prevent corrosion and shorting between conductors.

It has been found that hermetically sealing the inner chamber provides adequate protection to the imager and associated electronics during the steam autoclave process without the need for the double-walled housing containing a vacuum and the associated low-heat conducting support material, described in the aforementioned co-pending Ser. No. 08/018,053 (which is hereby fully incorporated by reference herein as though set forth in full). Thus, in this embodiment, a single walled outer housing is provided, and a vacuum is not maintained between the outer housing and the inner chamber. Nor is the low-heat conducting support material described used in this embodiment.

The inner surface 3d" of the second housing portion 3c" is preferably plated with a conductive material that extends from the female threads 241 around the inner lip thereof and into the groove 243 of conductive gasket 107. Alternatively, conductive paint or an inner foil could be used in lieu of plating in order to create the surface 3d". This conductive material functions to electrically couple the grounded cable shield 5a to chamber 219 through the inner portion 232 of the strain relief and the conductive gasket 107. The conductive gasket 107 is a canted spring design but a conductive elastomer O-ring is an alternative. The result is an EMI shield grounded to the cable shield 5a which encompasses the entirety of the electronics of the camera head 3.

In sum, a camera head with an inner electrically grounded hermetically (steam) sealed metal housing and an outer liquid sealed plastic housing is described which is configured to shield the imager and imager electronics from electro-magnetic interferences, to electrically isolate the head from the patient, and to be sterilizable using the steam autoclave process. While embodiments and applications of this invention have been shown and described, it should be apparent to those of ordinary skill in the art that may have embodiments are possible without departing from the spirit and scope of the subject invention.

For example, it should be appreciated that an endoscopic video camera head is possible and within the teachings of the subject invention which has a non-conductive and hermetically sealed outer enclosure with an internal conductive surface. The housing could be ceramic with a metal plated or coated inner surface. The distinctive difference between this embodiment and the previously described embodiments is that the outer enclosure is now hermetically sealed and the optical element is attached to it. The optical element is not attached to anything conductive. The inner enclosure consists of just a conductive plating for the purpose of EMI shielding.

Another example, also within the teachings of the subject invention, involves inclusion in the camera head of a memory chip for the purpose of keeping track of the number of procedures that have been performed. It is advantageous to store the number of times the camera head has been steam sterilized so that the unit can be scheduled for rebuilding or charged on a per-use basis. It is expected that the steam sterilization process will slowly degrade the unit and it is desirable to get it back for refurbishing on a regular basis. Two possible ways to determine the number of sterilization cycles are as follows:

1. Use of a sensor in the camera head that changes state at steam temperatures and can be reset electrically from the control unit; and
2. Counting one cycle each time the camera head is operated for 15 or 80 consecutive minutes. This information will be stored in the head mounted memory chip in accordance with the teachings of co-pending U.S. patent application Ser. No. 08/671,189.

Accordingly, the invention is not to be restricted, except as by the appended claims.

What is claimed is:

1. A video camera head adapted for coupling to a remote camera control unit through a cable having a shield, and also adapted for coupling to a separate endoscope, comprising:
    an imager;
    image electronics coupled to said imager;
    a non-conductive outer housing;
    an inner chamber within said outer housing having a conductive portion which substantially encloses said image and imager electronics;
    a first element for electrically coupling one end of a signal line in the cable to said image electronics;
    an optical element carried by said housing, and situated along an optical path extending through said housing and said inner chamber to said imager;
    a second element for electrically coupling the cable shield to said conductive portion of said inner chamber; and
    a first O-ring located near the optical element and the housing and a second O-ring located near the cable and the housing to seal any gaps in these respective areas such that said conductive portion of said inner chamber is substantially isolated from electrical contact with a human or a conductive fluid.

2. The camera head of claim 1 in which the conductive portion of the inner chamber comprises at least in part a conductive coating painted to an inner surface of the outer housing.

3. The camera head of claim 1 in which the conductive portion of the inner chamber comprises at least in part a conductive layer applied to an inner surface of the outer housing through plating.

4. The camera head of claim 1 in which the conductive portion of the inner chamber comprises at least in part a conductive layer applied to an inner surface of the outer housing through lamination.

5. The camera head of claim 1 further comprising a threaded ring for coupling the endoscope to the camera head contained entirely in said outer housing.

6. The camera head of claim 1 in which the optical element comprises a window made of sapphire that is brazed to a distal end of the conductive portion, which is made of titanium, of the inner chamber through at lest one circular joint.

7. The camera head of claim 1 in which the second element includes a strain relief.

8. The camera head of claim 1 wherein the leakage current passing through the head while the same is immersed in a conductive liquid with a voltage of 250 VAC applied thereto is less than about 50 microamps.

9. The camera head of claim 1 wherein the leakage current passing through the head while the same is immersed in a conductive liquid with a voltage of 2500 VAC applied thereto is less than about 25 microamps.

10. The camera head of claim 1 in which the conductive portion of said inner chamber is made of titanium.

11. The camera head of claim 1 in which the second element includes a two-part strain relief comprising a conductive portion substantially covered by a non-conductive portion.

12. The camera head of claim 11 in which the conductive portion of the two-part strain relief is electrically coupled to a conductive coating on an inner surface of said housing through a conductive gasket.

13. The camera head of claim 1 in which the conductive portion of the inner chamber comprises a bulkhead welded to an inner housing at a proximal end thereof.

14. The camera head of claim 13 in which the first element comprises glass-insulated feed-through conductors situated in the bulkhead.

15. The camera head of claim 1 in which the outer housing comprises a first part and a second part which are releasably engageable through a snap joint.

16. A video camera head adapted for coupling to a remote camera control unit through a cable having a shield, and also adapted for coupling to a separate endoscope, comprising:
    an imager;
    imager electronics coupled to said imager;
    a non-conductive outer housing;
    a hermetically-sealed inner chamber within said outer housing which substantially encloses said imager and imager electronics and which comprises an a conductive portion made of titanium, a window made of sapphire is brazed to a distal end of the conductive portion of the inner chamber through at lest one circular joint, wherein the window is situated along an optical path extending through said housing and said inner chamber to said imager;
    a first element for electrical coupling one end of a signal line in the cable to said imager electronics;
    a second element for electrically coupling said cable shield to said conductive portion of said inner chamber; and
    at least one seal carried by the housing such that said conductive portion of said inner chamber is substantially isolated from electrical contact with a human or a conductive fluid.

17. The camera head of claim 16 in which the conductive portion of the inner chamber comprises a bulkhead welded to a proximal end of an inner housing.

18. The camera head of claim 12 in which said first element comprises glass-insulated feed-through conductors situated in said bulkhead.

19. The camera head of claim 16 in which the outer housing is made of plastic.

20. A video camera head adapted for coupling to a remote camera control unit through a cable, and also adapted for coupling to a separate endoscope, comprising:

an imager;

imager electronics coupled to said imager;

a generally cylindrical non-conductive outer housing having a coaxially aligned first part and second part end releasably engageable through a snap joint for inserting and accessing said imager and imager electronics;

an inner chamber within said outer housing which substantially encloses said imager and imager electronics and which comprises an optical element affixed to a conductive portion, wherein the optical element is situated along an optical path extending through said housing and said inner chamber to said imager;

a first element for electrically coupling one end of a signal line in said cable to said imager electronics; and at least one seal carried by the housing such that said conductive portion of said inner chamber is substantially isolated from electrical contact with a human or conductive fluid.

21. A video camera head adapted for coupling to a remote camera control unit through a cable having a shield, and also adapted for coupling to an endoscope, comprising:

an imager;

imager electronics coupled to said imager;

a plastic outer housing;

an inner chamber within said housing which substantially encloses said imager and imager electronics, wherein said inner chamber comprises a conductive bulkhead welded to a proximal end of a conductive inner housing having a conductive portion, and a window situated along an optical path extending through said housing and inner chamber to said imager, wherein said window is brazed to a distal end of said inner housing through at least one circular joint, and wherein said outer housing comprises a first part and a second part which are releasable engageable through a snap joint;

a first element for electrically coupling one end of a signal line in said cable to said imager electronics;

a second element for electrically coupling said cable shield to said conductive portion of said inner chamber;

at least one seal carried by the housing in order to substantially isolate the conductive portion of said inner chamber form electrical contact with a patient or conductive fluid; and a third element situated entirely within said outer housing for coupling an endoscope to said imager along said optical path.

22. An endoscopic video camera system comprising:

a cable having a shield, and having a signal line with a first end and a second end;

a camera control unit coupled to the first end of said signal line; and the camera head of any of claims 1, 16, 21, wherein the second end of the signal line is coupled to the imager electronics through the first element, and the cable shield is coupled to the conductive portion of the inner chamber through the second element; and an endoscope coupled to the imager along said optical path through an optical coupler.

23. An endoscopic video camera system comprising:

a cable having a shield, and having a signal line with a first end and a second end;

a second element electrically coupled to the conductive portion of the inner chamber;

a camera control unit coupled to the first end of said signal line; and the camera head of claim 20, wherein the second end of the signal line is coupled to the imager electronics through the first element, and the cable shield is coupled to the conductive portion of the inner chamber through the second element; and an endoscope coupled to the imager along said optical path through an optical coupler.

* * * * *